US005532152A

United States Patent [19]
Cousens et al.

[11] Patent Number: 5,532,152
[45] Date of Patent: Jul. 2, 1996

[54] PLATELET-ACTIVATING FACTOR ACETYLHYDROLASE

[75] Inventors: Lawrence S. Cousens, Oakland, Calif.; Christine D. Eberhardt, Auburn, Wash.; Patrick Gray, Seattle, Wash.; Larry W. Tjoelker, Bothell, Wash.; Cheryl L. Wilder, Bellevue, Wash.; Hai Trong, Seattle, Wash.

[73] Assignee: ICOS Corporation, Bothell, Wash.

[21] Appl. No.: 470,187

[22] Filed: Jun. 6, 1995

Related U.S. Application Data

[63] Continuation of Ser. No. 133,803, Oct. 6, 1993, abandoned.
[51] Int. Cl.$^6$ .......................... C12N 9/18; C12N 15/55; C12N 5/10; C12N 1/15
[52] U.S. Cl. .................. 435/197; 435/240.2; 435/252.3; 435/320.1; 536/23.2; 536/23.5
[58] Field of Search .............................. 536/23.2, 24.31, 536/24.5, 23.5; 435/197, 198, 240.2, 252.3, 252.33, 320.1; 930/240

[56] References Cited

U.S. PATENT DOCUMENTS

| 5,019,508 | 5/1991 | Johnson et al. | 435/198 |
|---|---|---|---|
| 5,279,957 | 1/1994 | Gross | 536/23.2 |

FOREIGN PATENT DOCUMENTS

| 9313144 | 6/1993 | United Kingdom . |
| 9400413 | 1/1994 | United Kingdom . |
| WO95/00649 | 1/1995 | WIPO . |

OTHER PUBLICATIONS

Stafforini et al, "Human Plasma Platelet–activating Factor Acetylhydrolase" *J. Biol. Chem.* 262(9):4223–4230 (Mar. 1987).
Stafforini et al, "The Platelet–activating Factor Acetylhydrolase from Human Erythrocytes", *J. Biol. Chem.* 268(6):3857–3865 (Feb. 1993).
Brenner, "The Molecular Evolution of Genes and Proteins: A Tale of Two Serines", *Nature*, 334:528–530 (1988).
Capecchi, "Altering the Genome by Homologous Recombination", *Science*, 244:1288–1292 (1989).
Chapus et al., "Minireview on pancreatic lipase and colipase", *Biochemie*, 70:1223–1224 (1988).
Denizot et al., "PAF–Acether and Acetylhydrolase in Stool of Patients with Crohn's Disease", *Digestive Diseases and Sciences*, 37(3):432–437 (1992).
Handley et al., "Platelet Activating Factor and Inflammation in Atherogenesis: Targets for Drug Development", *Drug Dev. Res.*, 7:361–375 (1986).
Hattori et al., "Purification and Characterization of Bovine Brain Platelet–activating Factor Acetylhydrolase", *J. Biol. Chem.*, 268(25):18748–18753 (1993).
Heuer et al., "Current status of PAF antagonists", *Clin. Exp. Allergy*, 22:980–983 (1992).

Kald et al., "Release of Platelet–Activating Factor in Acute Experimental Pancreatitis", *Pancreas*, 8(4):440–442 (1993).
Lindsberg et al., "Evidence for Platelet–Activating Factor as a Novel Mediator in Experimental Stroke in Rabbits", *Stroke*, 21:1452–1457 (1990).
Lindsberg et al., "Platelet–activating Factor in Stroke and Brain Injury", *Ann Neurol.*, 30:117–129 (1991).
Matsuzaki et al., "PAF acetylhydrolase activities in human systemic lupus erythematosus and lupus–pronemice", *Clinica Chimica Acta*, 210:139–144 (1992).
Mezzano et al., "Detection of Platelet–Activating Factor in Plasma of Patients With Streptococcal Nephritis", *J. Am. Soc. Nephrol.*, 4:235–242 (1993).
Miwa et al., "Characterization of Serum Platelet–activating Factor (PAF) Acetylhydrolase", *J. Clin. Invest.*, 82:1983–1991 (1988).
Rabinovici et al., "Platelet Activating Factor Mediates Interleukin–2–induced Lung Injury in the Rat", *J. Clin. Invest.*, 89:1669–1673 (1992).
Satoh et al., "Platelet–activating Factor (PAF) Stimulates the Production of PAF Acetylhydrolase by the Human Hepatoma Cell Line, HepG2", *J. Clin. Invest.*, 87:476–481 (1991).
Satoh et al., "Platelet-Activating Factor Acetylhydrolase in Plasma Lipoproteins From Patients with Ischemic Stroke", *Stroke*, 23:1090–1092 (1992).
Stafforini et al., "Human Macrophages Secrete Platelet–activating Factor Acetylhydrolase", *J. Biol. Chem.*, 265(17):9682–9687 (1990).
Stremler et al., "Human Plasma Platelet–activating Factor Acetylhydrolase", *J. Biol. Chem.*, 266(17):11095–11113 (1991).
Tarbet et al., "Liver Cells Secrete the Plasma Form of Platelet–activating Factor Acetylhydrolase", *J. Biol. Chem.*, 266(25):16667–16673 (1991).
Venable et al., "Platelet–activating factor: a phospholipid autacoid with diverse actions", *J. Lipid Res.*, 34:691–701 (1993).
Wada et al., "Codon Usage Tabulated from the GenBank Genetic Sequence Data", *Nuc. Acids Res.*, 19S:1981–1986 (1991).
Zarco et al., "Involvement of platelet–activating factor and tumour necrosis factor in the pathogenesis of joint inflammation in rabbits", *Clin. Exp. Immunol.*, 88:318–323 (1992).
Stafforini et al., "Platelet-Activating Factor Acetylhydrolase Activity in Human Tissues and Blood Cells", *Lipids*, 26(12):979–985 (1991).

*Primary Examiner*—Stephen G. Walsh
*Attorney, Agent, or Firm*—Marshall, O'Toole, Gerstein, Murray & Borun

[57] ABSTRACT

The present invention provides purified and isolated polynucleotide sequences encoding human plasma platelet-activating factor acetylhydrolase. Also provided are materials and methods for the recombinant production of platelet-activating factor acetylhydrolase products which are expected to be useful in regulating pathological inflammatory events.

15 Claims, 2 Drawing Sheets

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 17 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO:1:

```
Phe Lys Asp Leu Gly Glu Glu Asn Phe Lys Ala Leu Val Leu Ile Ala
1               5                   10                  15
Phe
```

( 2 ) INFORMATION FOR SEQ ID NO:2:

( i ) SEQUENCE CHARACTERISTICS:
        ( A ) LENGTH: 16 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO:2:

```
Ile Gln Val Leu Met Ala Ala Ala Ser Phe Gly Gln Thr Lys Ile Pro
1               5                   10                  15
```

( 2 ) INFORMATION FOR SEQ ID NO:3:

( i ) SEQUENCE CHARACTERISTICS:

(A) LENGTH: 11 amino acids
(B) TYPE: amino acid
(D) TOPOLOGY: linear (ii) MOLECULE TYPE: peptide (xi) SEQUENCE DESCRIPTION: SEQ ID NO:3:

Met Lys Pro Leu Val Val Phe Val Leu Gly Gly
1               5                   10

(2) INFORMATION FOR SEQ ID NO:4:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: Modified-site
(B) LOCATION: group(13, 21, 27)
(C) OTHER INFORMATION: /note="The nucleotide at each of these positions is an inosine."

(xi) SEQUENCE DESCRIPTION: SEQ ID NO:4:

ACATGAATTC GGNATCYTTG NGTYTGNCCR AA 32

(2) INFORMATION FOR SEQ ID NO:5:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:5:

TATTTCTAGA AGTGTGGTGG AACTCGCTGG 30

(2) INFORMATION FOR SEQ ID NO:6:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:6:

CGATGAATTC AGCTTGCAGC AGCCATCAGT AC 32

(2) INFORMATION FOR SEQ ID NO:7:

(i) SEQUENCE CHARACTERISTICS:
(A) LENGTH: 1520 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 162..1484

(xi) SEQUENCE DESCRIPTION: SEQ ID NO:7:

GCTGGTCGGA GGCTCGCAGT GCTGTCGGCG AGAAGCAGTC GGGTTTGGAG CGCTTGGGTC 60

```
GCGTTGGTGC GCGGTGGAAC GCGCCCAGGG ACCCCAGTTC CCGCGAGCAG CTCCGCGCCG    120

CGCCTGAGAG ACTAAGCTGA AACTGCTGCT CAGCTCCCAA G ATG GTG CCA CCC        173
                                              Met Val Pro Pro
                                               1

AAA TTG CAT GTG CTT TTC TGC CTC TGC GGC TGC CTG GCT GTG GTT TAT    221
Lys Leu His Val Leu Phe Cys Leu Cys Gly Cys Leu Ala Val Val Tyr
 5           10              15                  20

CCT TTT GAC TGG CAA TAC ATA AAT CCT GTT GCC CAT ATG AAA TCA TCA    269
Pro Phe Asp Trp Gln Tyr Ile Asn Pro Val Ala His Met Lys Ser Ser
             25              30                  35

GCA TGG GTC AAC AAA ATA CAA GTA CTG ATG GCT GCT GCA AGC TTT GGC    317
Ala Trp Val Asn Lys Ile Gln Val Leu Met Ala Ala Ala Ser Phe Gly
         40              45                  50

CAA ACT AAA ATC CCC CGG GGA AAT GGG CCT TAT TCC GTT GGT TGT ACA    365
Gln Thr Lys Ile Pro Arg Gly Asn Gly Pro Tyr Ser Val Gly Cys Thr
     55              60                  65

GAC TTA ATG TTT GAT CAC ACT AAT AAG GGC ACC TTC TTG CGT TTA TAT    413
Asp Leu Met Phe Asp His Thr Asn Lys Gly Thr Phe Leu Arg Leu Tyr
 70              75                  80

TAT CCA TCC CAA GAT AAT GAT CGC CTT GAC ACC CTT TGG ATC CCA AAT    461
Tyr Pro Ser Gln Asp Asn Asp Arg Leu Asp Thr Leu Trp Ile Pro Asn
 85              90                  95                  100

AAA GAA TAT TTT TGG GGT CTT AGC AAA TTT CTT GGA ACA CAC TGG CTT    509
Lys Glu Tyr Phe Trp Gly Leu Ser Lys Phe Leu Gly Thr His Trp Leu
             105             110                 115

ATG GGC AAC ATT TTG AGG TTA CTC TTT GGT TCA ATG ACA ACT CCT GCA    557
Met Gly Asn Ile Leu Arg Leu Leu Phe Gly Ser Met Thr Thr Pro Ala
         120             125                 130

AAC TGG AAT TCC CCT CTG AGG CCT GGT GAA AAA TAT CCA CTT GTT GTT    605
Asn Trp Asn Ser Pro Leu Arg Pro Gly Glu Lys Tyr Pro Leu Val Val
     135             140                 145

TTT TCT CAT GGT CTT GGG GCA TTC AGG ACA CTT TAT TCT GCT ATT GGC    653
Phe Ser His Gly Leu Gly Ala Phe Arg Thr Leu Tyr Ser Ala Ile Gly
 150             155                 160

ATT GAC CTG GCA TCT CAT GGG TTT ATA GTT GCT GCT GTA GAA CAC AGA    701
Ile Asp Leu Ala Ser His Gly Phe Ile Val Ala Ala Val Glu His Arg
 165             170                 175                 180

GAT AGA TCT GCA TCT GCA ACT TAC TAT TTC AAG GAC CAA TCT GCT GCA    749
Asp Arg Ser Ala Ser Ala Thr Tyr Tyr Phe Lys Asp Gln Ser Ala Ala
             185             190                 195

GAA ATA GGG GAC AAG TCT TGG CTC TAC CTT AGA ACC CTG AAA CAA GAG    797
Glu Ile Gly Asp Lys Ser Trp Leu Tyr Leu Arg Thr Leu Lys Gln Glu
         200             205                 210

GAG GAG ACA CAT ATA CGA AAT GAG CAG GTA CGG CAA AGA GCA AAA GAA    845
Glu Glu Thr His Ile Arg Asn Glu Gln Val Arg Gln Arg Ala Lys Glu
     215             220                 225

TGT TCC CAA GCT CTC AGT CTG ATT CTT GAC ATT GAT CAT GGA AAG CCA    893
Cys Ser Gln Ala Leu Ser Leu Ile Leu Asp Ile Asp His Gly Lys Pro
 230             235                 240

GTG AAG AAT GCA TTA GAT TTA AAG TTT GAT ATG GAA CAA CTG AAG GAC    941
Val Lys Asn Ala Leu Asp Leu Lys Phe Asp Met Glu Gln Leu Lys Asp
 245             250                 255                 260

TCT ATT GAT AGG GAA AAA ATA GCA GTA ATT GGA CAT TCT TTT GGT GGA    989
Ser Ile Asp Arg Glu Lys Ile Ala Val Ile Gly His Ser Phe Gly Gly
             265             270                 275

GCA ACG GTT ATT CAG ACT CTT AGT GAA GAT CAG AGA TTC AGA TGT GGT    1037
Ala Thr Val Ile Gln Thr Leu Ser Glu Asp Gln Arg Phe Arg Cys Gly
         280             285                 290

ATT GCC CTG GAT GCA TGG ATG TTT CCA CTG GGT GAT GAA GTA TAT TCC    1085
```

```
              Ile Ala Leu Asp Ala Trp Met Phe Pro Leu Gly Asp Glu Val Tyr Ser
                      295                 300                 305

AGA ATT CCT CAG CCC CTC TTT TTT ATC AAC TCT GAA TAT TTC CAA TAT              1133
Arg Ile Pro Gln Pro Leu Phe Phe Ile Asn Ser Glu Tyr Phe Gln Tyr
    310                 315                 320

CCT GCT AAT ATC ATA AAA ATG AAA AAA TGC TAC TCA CCT GAT AAA GAA              1181
Pro Ala Asn Ile Ile Lys Met Lys Lys Cys Tyr Ser Pro Asp Lys Glu
325                 330                 335                 340

AGA AAG ATG ATT ACA ATC AGG GGT TCA GTC CAC CAG AAT TTT GCT GAC              1229
Arg Lys Met Ile Thr Ile Arg Gly Ser Val His Gln Asn Phe Ala Asp
                345                 350                 355

TTC ACT TTT GCA ACT GGC AAA ATA ATT GGA CAC ATG CTC AAA TTA AAG              1277
Phe Thr Phe Ala Thr Gly Lys Ile Ile Gly His Met Leu Lys Leu Lys
            360                 365                 370

GGA GAC ATA GAT TCA AAT GTA GCT ATT GAT CTT AGC AAC AAA GCT TCA              1325
Gly Asp Ile Asp Ser Asn Val Ala Ile Asp Leu Ser Asn Lys Ala Ser
        375                 380                 385

TTA GCA TTC TTA CAA AAG CAT TTA GGA CTT CAT AAA GAT TTT GAT CAG              1373
Leu Ala Phe Leu Gln Lys His Leu Gly Leu His Lys Asp Phe Asp Gln
    390                 395                 400

TGG GAC TGC TTG ATT GAA GGA GAT GAT GAG AAT CTT ATT CCA GGG ACC              1421
Trp Asp Cys Leu Ile Glu Gly Asp Asp Glu Asn Leu Ile Pro Gly Thr
405                 410                 415                 420

AAC ATT AAC ACA ACC AAT CAA CAC ATC ATG TTA CAG AAC TCT TCA GGA              1469
Asn Ile Asn Thr Thr Asn Gln His Ile Met Leu Gln Asn Ser Ser Gly
                425                 430                 435

ATA GAG AAA TAC AAT  TAGGATTAAA ATAGGTTTTT TAAAAAAAAA AAAAAA                  1520
Ile Glu Lys Tyr Asn
                440
```

(2) INFORMATION FOR SEQ ID NO:8:

(i) SEQUENCE CHARACTERISTICS:
        (A) LENGTH: 441 amino acids
        (B) TYPE: amino acid
        (D) TOPOLOGY: linear     (ii) MOLECULE TYPE: protein     (xi) SEQUENCE DESCRIPTION: SEQ ID NO:8:

```
Met Val Pro Pro Lys Leu His Val Leu Phe Cys Leu Cys Gly Cys Leu
1               5                   10                  15

Ala Val Val Tyr Pro Phe Asp Trp Gln Tyr Ile Asn Pro Val Ala His
                20                  25                  30

Met Lys Ser Ser Ala Trp Val Asn Lys Ile Gln Val Leu Met Ala Ala
            35                  40                  45

Ala Ser Phe Gly Gln Thr Lys Ile Pro Arg Gly Asn Gly Pro Tyr Ser
        50                  55                  60

Val Gly Cys Thr Asp Leu Met Phe Asp His Thr Asn Lys Gly Thr Phe
65                  70                  75                  80

Leu Arg Leu Tyr Tyr Pro Ser Gln Asp Asn Asp Arg Leu Asp Thr Leu
                85                  90                  95

Trp Ile Pro Asn Lys Glu Tyr Phe Trp Gly Leu Ser Lys Phe Leu Gly
                100                 105                 110

Thr His Trp Leu Met Gly Asn Ile Leu Arg Leu Leu Phe Gly Ser Met
            115                 120                 125

Thr Thr Pro Ala Asn Trp Asn Ser Pro Leu Arg Pro Gly Glu Lys Tyr
        130                 135                 140

Pro Leu Val Val Phe Ser His Gly Leu Gly Ala Phe Arg Thr Leu Tyr
145                 150                 155                 160
```

| | | | | | | | | | | | | | | |
|---|---|---|---|---|---|---|---|---|---|---|---|---|---|---|
| Ser | Ala | Ile | Gly | Ile<br>165 | Asp | Leu | Ala | Ser | His<br>170 | Gly | Phe | Ile | Val | Ala Ala<br>175 |
| Val | Glu | His | Arg<br>180 | Asp | Arg | Ser | Ala | Ser<br>185 | Ala | Thr | Tyr | Tyr | Phe<br>190 | Lys Asp |
| Gln | Ser | Ala<br>195 | Ala | Glu | Ile | Gly | Asp<br>200 | Lys | Ser | Trp | Leu | Tyr<br>205 | Leu | Arg Thr |
| Leu | Lys<br>210 | Gln | Glu | Glu | Glu | Thr<br>215 | His | Ile | Arg | Asn | Glu<br>220 | Gln | Val | Arg Gln |
| Arg<br>225 | Ala | Lys | Glu | Cys | Ser<br>230 | Gln | Ala | Leu | Ser | Leu<br>235 | Ile | Leu | Asp | Ile Asp<br>240 |
| His | Gly | Lys | Pro | Val<br>245 | Lys | Asn | Ala | Leu | Asp<br>250 | Leu | Lys | Phe | Asp | Met Glu<br>255 |
| Gln | Leu | Lys | Asp<br>260 | Ser | Ile | Asp | Arg | Glu<br>265 | Lys | Ile | Ala | Val | Ile<br>270 | Gly His |
| Ser | Phe | Gly<br>275 | Gly | Ala | Thr | Val | Ile<br>280 | Gln | Thr | Leu | Ser | Glu<br>285 | Asp | Gln Arg |
| Phe | Arg<br>290 | Cys | Gly | Ile | Ala | Leu<br>295 | Asp | Ala | Trp | Met | Phe<br>300 | Pro | Leu | Gly Asp |
| Glu<br>305 | Val | Tyr | Ser | Arg | Ile<br>310 | Pro | Gln | Pro | Leu | Phe<br>315 | Phe | Ile | Asn | Ser Glu<br>320 |
| Tyr | Phe | Gln | Tyr | Pro<br>325 | Ala | Asn | Ile | Ile | Lys<br>330 | Met | Lys | Lys | Cys | Tyr Ser<br>335 |
| Pro | Asp | Lys | Glu<br>340 | Arg | Lys | Met | Ile | Thr<br>345 | Ile | Arg | Gly | Ser | Val<br>350 | His Gln |
| Asn | Phe | Ala<br>355 | Asp | Phe | Thr | Phe | Ala<br>360 | Thr | Gly | Lys | Ile | Ile<br>365 | Gly | His Met |
| Leu | Lys<br>370 | Leu | Lys | Gly | Asp | Ile<br>375 | Asp | Ser | Asn | Val | Ala<br>380 | Ile | Asp | Leu Ser |
| Asn<br>385 | Lys | Ala | Ser | Leu | Ala<br>390 | Phe | Leu | Gln | Lys | His<br>395 | Leu | Gly | Leu | His Lys<br>400 |
| Asp | Phe | Asp | Gln | Trp<br>405 | Asp | Cys | Leu | Ile | Glu<br>410 | Gly | Asp | Asp | Glu | Asn Leu<br>415 |
| Ile | Pro | Gly | Thr<br>420 | Asn | Ile | Asn | Thr | Thr<br>425 | Asn | Gln | His | Ile | Met<br>430 | Leu Gln |
| Asn | Ser | Ser<br>435 | Gly | Ile | Glu | Lys | Tyr<br>440 | Asn | | | | | | |

( 2 ) INFORMATION FOR SEQ ID NO:9:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear     ( i i ) MOLECULE TYPE: DNA     ( x i ) SEQUENCE DESCRIPTION: SEQ ID NO:9:

TATTCTAGAA TTATGATACA AGTATTAATG GCTGCTGCAA G     41

( 2 ) INFORMATION FOR SEQ ID NO:10:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear     ( i i ) MOLECULE TYPE: DNA (x i) SEQUENCE DESCRIPTION: SEQ ID NO:10:

ATTGATATCC TAATTGTATT TCTCTATTCC TG                    32

(2) INFORMATION FOR SEQ ID NO:11:

(i) SEQUENCE CHARACTERISTICS:
        (A) LENGTH: 5 amino acids
        (B) TYPE: amino acid
        (D) TOPOLOGY: linear     (ii) MOLECULE TYPE: peptide     (x i) SEQUENCE DESCRIPTION: SEQ ID NO:11:

Gly  Xaa  Ser  Xaa  Gly
    1                      5

PLATELET-ACTIVATING FACTOR ACETYLHYDROLASE

This is a Rule 62 file wrapper continuation of U.S. patent application Ser. No. 08/133,803, filed Oct. 6, 1993, now abandoned.

FIELD OF THE INVENTION

The present invention relates generally to platelet-activating factor acetylhydrolase and more specifically to novel purified and isolated polynucleotides encoding human plasma platelet-activating factor acetylhydrolase, to the platelet-activating factor acetylhydrolase products encoded by the polynucleotides, to materials and methods for the recombinant production of platelet-activating factor acetylhydrolase products and to antibody substances specific for platelet-activating factor acetylhydrolase.

BACKGROUND

Platelet-activating factor (PAF) is a biologically active phospholipid synthesized by various cell types. In vivo and at normal concentrations of $10^{-10}$ to $10^{-9}$M, PAF activates target cells such as platelets and neutrophils by binding to specific G protein-coupled cell surface receptors [Venable et al., *J. Lipid Res.*, 34: 69 1–701 (1993)]. PAF has the structure 1-O-alkyl-2-acetyl-sn-glycero-3-phosphocholine. For optimal biological activity, the sn-1 position of the PAF glycerol backbone must be in an ether linkage with a fatty alcohol and the sn-3 position must have a phosphocholine head group.

PAF functions in normal physiological processes (e.g., inflammation, hemostasis and parturition) and is implicated in pathological inflammatory responses (e.g., asthma, anaphylaxis, septic shock and arthritis) [Venable et al., supra, and Lindsberg et al., *Ann. Neurol.*, 30: 117–129 (1991)]. The likelihood of PAF involvement in pathological responses has prompted attempts to modulate the activity of PAF and the major or focus of these attempts has been the development of antagonists of PAF activity which interfere with binding of PAF to cell surface receptors. See, for example, Heuer et al., *Clin. Exp. Allergy*, 22: 980–983 (1992).

The synthesis and secretion of PAF as well as its degradation and clearance appear to be tightly controlled. To the extent that pathological inflammatory actions of PAF result from a failure of PAF regulatory mechanisms giving rise to excessive production, inappropriate production or lack of degradation, an alternative means of modulating the activity of PAF would involve mimicing or augmenting the natural process by which resolution of inflammation occurs. Macrophages [Stafforini et al., *J. Biol. Chem.*, 265(17): 9682–9687 (1990)], hepatocytes and the human hepatoma cell line HepG2 [Satoh et al., *J. Clin. Invest.*, 87: 476–481 (1991) and Tarbet et at., *J. Biol. Chem.*, 266(25): 16667–16673 (1991)] have been reported to release an enzymatic activity, PAF acetylhydrolase (PAF-AH), that inactivates PAF. In addition to inactivating PAF, PAF-AH also inactivates oxidatively fragmented phospholipids such as products of the arachidonic acid cascade that mediate inflammation. See, Stremler et al., *J. Biol. Chem.*, 266(17): 11095–11103 (1991). The inactivation of PAF by PAF-AH occurs primarily by hydrolysis of the PAF sn-2 acetyl group and PAF-AH metabolizes oxidatively fragmented phospholipids by removing sn-2 acyl groups. Two types of PAF-AH have been identified: cytoplasmic forms found in a variety of cell types and tissues such as endothelial cells and erythrocytes, and an extracellular form found in plasma and serum. Plasma PAF-AH does not hydrolyze intact phospholipids except for PAF and this substrate specificity allows the enzyme to circulate in vivo in a fully active state without adverse effects. The plasma PAF-AH appears to account for all of the PAF degradation in human blood ex vivo [Stafforini et al., *J. Biol. Chem.*, 262(9): 4223–4230 (1987)].

While the cytoplasmic and plasma forms of PAF-AH appear to have identical substrate specificity, plasma PAF-AH has biochemical characteristics which distinguish it from cytoplasmic PAF-AH and from other characterized lipases. Specifically, plasma PAF-AH is associated with lipoprotein particles, is inhibited by diisopropyl fluorophosphate, is not affected by calcium ions, is relatively insensitive to proteolysis, and has an apparent molecular weight of 43,000 daltons. See, Stafforini et al. (1987), supra. The same Stafforini et al. article describes a procedure for partial purification of PAF-AH from human plasma and the amino acid composition of the plasma material obtained by use of the procedure. Cytoplasmic PAF-AH has been purified from erythrocytes as reported in Stafforini et al., *J. Biol. Chem.*, 268(6): 3857–3865 (1993) and ten amino terminal residues of cytoplasmic PAF-AH are also described in the article. Hattori et al., *J. Biol. Chem.*, 268(25): 18748–18753 (1993) describes the purification of cytoplasmic PAF-AH from bovine brain. To date, no nucleotide sequence for either plasma or cytoplasmic forms of PAF-AH has been published.

The recombinant production of PAF-AH would make possible the use of exogenous PAF-AH to mimic or augment normal processes of resolution of inflammation in vivo. The administration of PAF-AH would provide a physiological advantage over administration of PAF receptor antagonists because PAF-AH is a product normally found in plasma. Moreover, because PAF receptor antagonists which are structurally related to PAF inhibit native PAF-AH activity, the desirable metabolism of PAF and of oxidatively fragmented phospholipids is thereby prevented. Thus, the inhibition of PAF-AH activity by PAF receptor antagonists counteracts the competitive blockade of the PAF receptor by the antagonists. See, Stremler et al., supra.

There thus exists a need in the art to identify and isolate polynucleotide sequences encoding human plasma PAF-AH, to develop materials and methods useful for the recombinant production of PAF-AH and to generate reagents for the detection of PAF-AH in plasma.

SUMMARY OF THE INVENTION

The present invention provides novel purified and isolated polynucleotides (i.e., DNA and RNA) encoding human plasma PAF-AH or enzymatically active fragments thereof. Preferred DNA sequences of the invention include genomic and cDNA sequences as well as wholly or partially chemically synthesized DNA sequences. The DNA sequence encoding PAF-AH that is set out in SEQ ID NO: 7 and DNA sequences which hybridize to the noncoding strand thereof under standard stringent conditions or which would hybridize but for the redundancy of the genetic code, are contemplated by the invention. Also contemplated by the invention are biological replicas (i.e., copies of isolated DNA sequences made in vivo or in vitro) of DNA sequences of the invention. Autonomously replicating recombinant constructions such as plasmid and viral DNA vectors incorporating PAF-AH sequences and especially vectors wherein DNA encoding PAF-AH is operatively linked to an endogenous or exogenous expression control DNA sequence and a transcription terminator are also provided.

According to another aspect of the invention, procaryotic or eucaryotic host cells are stably transformed with DNA sequences of the invention in a manner allowing the desired PAF-AH to be expressed therein. Host cells expressing PAF-AH products can serve a variety of useful purposes. Such cells constitute a valuable source of immunogen for the development of antibody substances specifically immunoreactive with PAF-AH. Host cells of the invention are conspicuously useful in methods for the large scale production of PAF-AH wherein the cells are grown in a suitable culture medium and the desired polypeptide products are isolated from the cells or from the medium in which the cells are grown by, for example, immunoaffinity purification.

A non-immunological method contemplated by the invention for purifying PAF-AH from plasma includes the following steps: (a) isolating low density lipoprotein particles; (b) solubilizing said low density lipoprotein particles in a buffer comprising 10 mM CHAPS to generate a first PAF-AH enzyme solution; (c) applying said first PAF-AH enzyme solution to a DEAE anion exchange column; (d) washing said DEAE anion exchange column using an approximately pH 7.5 buffer comprising 1 mM CHAPS; (e) eluting PAF-AH enzyme from said DEAE anion exchange column in fractions using approximately pH 7.5 buffers comprising a gradient of 0 to 0.5M NaCl; (f) pooling fractions eluted from said DEAE anion exchange column having PAF-AH enzymatic activity; (g) adjusting said pooled, active fractions from said DEAE anion exchange column to 10 mM CHAPS to generate a second PAF-AH enzyme solution; (h) applying said second PAF-AH enzyme solution to a blue dye ligand affinity column; (i) eluting PAF-AH enzyme from said blue dye ligand affinity column using a buffer comprising 10 mm CHAPS and a chaotropic salt; (j) applying the eluate from said blue dye ligand affinity column to a Cu ligand affinity column; (k) eluting PAF-AH enzyme from said Cu ligand affinity column using a buffer comprising 10 mm CHAPS and imidazole; (l) subjecting the eluate from said Cu ligand affinity column to SDS-PAGE; and (m) isolating ~44 kDa PAFAH enzyme from the SDS-polyacrylamide gel. Preferably, the buffer of step (b) is 25 mM Tris-HCl, 10 mM CHAPS, pH 7.5; the buffer of step (d) is 25 mM Tris-HCl, 1 mM CHAPS; the column of step (h) is a Blue SEPHAROSE® Fast Flow column; the buffer of step (i) is 25 mM Tris-HCl, 10 mM CHAPS, 0.5M KSCN, pH 7.5; the column of step (j) is a Cu Chelating SEPHAROSE® column; and the buffer of step (k) is 25 mM Tris-HCl, 10 mM CHAPS, 0.5M NaCl, 50 mM imidazole at a pH in a range of about pH 7.5–8.0.

A method contemplated by the invention for purifying enzymatically-active PAF-AH from E. coli producing PAF-AH includes the steps of: (a) preparing a centrifugation supernatant from lysed E. coli producing PAF-AH enzyme; (b) applying said centrifugation supernatant to a blue dye ligand affinity column; (c) eluting PAF-AH enzyme from said blue dye ligand affinity column using a buffer comprising 10 mM CHAPS and a chaotropic salt; (d) applying said eluate from said blue dye ligand affinity column to a Cu ligand affinity column; and (e) eluting PAF-AH enzyme from said Cu ligand affinity column using a buffer comprising 10 mM CHAPS and imidazole. Preferably, the column of step (b) is a Blue SEPHAROSE® Fast Flow column; the buffer of step (c) is 25 mM Tris-HCl, 10 mM CHAPS, 0.5M KSCN, pH. 7.5; the column of step (d) is a Cu Chelating SEPHAROSE® column; and the buffer of step (e) is 25 mM Tris-HCl, 10 mM CHAPS, 0.5M NaCl, 100 mM imidazole, pH 7.5.

PAF-AH products may be obtained as isolates from natural cell sources or may be chemically synthesized, but are preferably produced by recombinant procedures involving procaryotic or eucaryotic host cells of the invention. PAF-AH products having part or all of the amino acid sequence set out in SEQ ID NO: 8 are contemplated. The use of mammalian host cells is expected to provide for such post-translational modifications (e.g., myristolation, glycosylation, truncation, lipidation and tyrosine, serine or threonine phosphorylation) as may be needed to confer optimal biological activity on recombinant expression products of the invention. PAF-AH products of the invention may be full length polypeptides, fragments or variants. Variants may comprise PAF-AH analogs wherein one or more of the specified (i.e., naturally encoded) amino acids is deleted or replaced or wherein one or more nonspecified amino acids are added: (1) without loss of one or more of the enzymatic activities or immunological characteristics specific to PAF-AH; or (2) with specific disablement of a particular biological activity of PAF-AH. Proteins or other molecules that bind to PAF-AH may be used to modulate its activity.

Also comprehended by the present invention are antibody substances (e.g., monoclonal and polyclonal antibodies, single chain antibodies, chimeric antibodies, CDR-grafted antibodies and the like) and other binding proteins specific for PAF-AH. Proteins or other molecules which specifically bind to PAF-AH (e.g., lipids or small molecules) can be identified using PAF-AH isolated from plasma, recombinant PAF-AH, PAF-AH variants or cells expressing such products. Binding proteins are useful, in turn, in compositions for immunization as well as for purifying PAF-AH, and are useful for detection or quantification of PAF-AH in fluid and tissue samples by known immunological procedures. Anti-idiotypic antibodies specific for PAF-AH-specific antibody substances are also contemplated.

The scientific value of the information contributed through the disclosures of DNA and amino acid sequences of the present invention is manifest. As one series of examples, knowledge of the sequence of a cDNA for PAF-AH makes possible the isolation by DNA/DNA hybridization of genomic DNA sequences encoding PAF-AH and specifying PAF-AH expression control regulatory sequences such as promoters, operators and the like. DNA/DNA hybridization procedures carried out with DNA sequences of the invention under stringent conditions are likewise expected to allow the isolation of DNAs encoding allelic variants of PAF-AH, other structurally related proteins sharing one or more of the biochemical and/or immunological properties of PAF-AH, and non-human species proteins homologous to PAF-AH. The DNA sequence information provided by the present invention also makes possible the development, by homologous recombination or "knockout" strategies [see, e.g., Kapecchi, Science, 244: 1288–1292 (1989)], of rodents that fail to express a functional PAF-AH enzyme or that express a variant PAF-AH enzyme. Polynucleotides of the invention when suitably labelled are useful in hybridization assays to detect the capacity of cells to synthesize PAF-AH. Polynucleotides of the invention may also be the basis for diagnostic methods useful for identifying a genetic alteration(s) in the PAF-AH locus that underlies a disease state or states. Also made available by the invention are anti-sense polynucleotides relevant to regulating expression of PAF-AH by those cells which ordinarily express the same.

Administration of PAF-AH preparations of the invention to mammalian subjects, especially humans, for the purpose of ameliorating pathological inflammatory conditions is contemplated. Based on implication of the involvement of PAF in pathological inflammatory conditions, the administration of PAF-AH is indicated, for example, in treatment of asthma [Miwa et al., *J. Clin. Invest.,* 82: 1983–1991 (1988)], anaphylaxis [Venable et al., supra], shock [Venable et al., supra], reperfusion injury and CNS ischemia [Lindsberg et al. (1991), supra], antigen-induced arthritis [Zarco et al., *Clin. Exp. Immunol.,* 88:318–323 (1992)], atherogenesis [Handley et al., *Drug Dev. Res.,* 7: 361–375 (1986)], Crohn's disease [Denizot et al., *Digestive Diseases and Sciences,* 37(3): 432–437 (1992)], ischemic bowel necrosis (Denizot et al., supra), ulcerative colitis (Denizot et al., supra), ischemic stroke [Satoh et al., Stroke, 23: 1090–1092 (1992)], ischemic brain injury [Lindsberg et al., *Stroke,* 21: 1452–1457 (1990) and Lindsberg et al. (1991), supra], systemic lupus erythematosus [Matsuzaki et al., *Clinica Chimica Acta,* 210:139–144 (1992)], acute pancreatitis [Kald et al., *Pancreas,* 8(4): 440–442 (1993)], septicemia (Kald et al., supra), acute post streptococcal glomerulonephritis [Mezzano et al., *J. Am. Soc. Nephrol.,* 4: 235–242 (1993)] and pulmonary edema resulting from IL-2 therapy [Rabinovici et al., *J. Clin. Invest.,* 89: 1669–1673 (1992)]. Animal models for many of the foregoing pathological conditions have been described in the art. For example, a rabbit model for arthritis is described in Zarco et al., supra; a rabbit model for stroke is described in Lindsberg et al. (1990), supra; a mouse model for lupus is described in Matsuzaki et al., supra; a rat model for acute pancreatitis is described in Kald et al., supra: and a rat model for pulmonary edema resulting from IL-2 therapy is described in Rabinovici et al., supra. Therapeutic compositions contemplated by the invention include PAF-AH and a physiologically acceptable diluent or carrier and may also include other agents having anti-inflammatory effects. Dosage amounts indicated would be sufficient to supplement endogenous PAF-AH activity and to inactivate pathological amounts of PAF.

BRIEF DESCRIPTION OF THE DRAWING

Numerous other aspects and advantages of the present invention will be apparent upon consideration of the following detailed description thereof, reference being made to the drawing wherein.

DETAILED DESCRIPTION

The following examples illustrate the invention. Example 1 presents a novel method for the purification of PAF-AH from human plasma. Example 2 describes amino acid microsequencing of the purified human plasma PAF-AH. The cloning of a full length cDNA encoding human plasma PAF-AH is described in Example 3. Example 4 presents the results of an assay evidencing the enzymatic activity of recombinant PAF-AH transiently expressed in COS 7 cells. Example 5 describes the expression of human PAF-AH in *E. coli.* Example 6 presents a protocol for purification of recombinant PAF-AH from *E. coli* and assays confirming its enzymatic activity. Results of a Northern blot assay for expression of human plasma PAF-AH RNA in various tissues and cell lines are presented in Example 7.

EXAMPLE 1

PAF-AH was purified from human plasma in order to provide material for amino acid sequencing.

A. Optimization of Purification Conditions

Initially, low density lipoprotein (LDL) particles were precipitated from plasma with phosphotungstate and solubilized in 0.1% Tween 20 and subjected to chromatography on a DEAE column (Pharmacia, Uppsala, Sweden) according to the method of Stafforini et al. (1987), supra, but inconsistent elution of PAF-AH activity from the DEAE column required reevaluation of the solubilization and subsequent purification conditions.

Tween 20, CHAPS (Pierce Chemical Co., Rockford, Ill.) and octyl glucoside were evaluated by centrifugation and gel filtration chromatography for their ability to solubilize LDL particles. CHAPS provided 25% greater recovery of solubilized activity than Tween 20 and 300% greater recovery than octyl glucoside. LDL precipitate solubilized with 10 mM CHAPS was then fractionated on a DEAE SEPHAROSE® Fast Flow column (an anion exchange column; Pharmacia) with buffer containing 1 mM CHAPS to provide a large pool of partially purified PAF-AH ("the DEAE pool") for evaluation of additional columns.

The DEAE pool was used as starting material to test a variety of chromatography columns for utility in further purifying the PAF-AH activity. The columns tested included: Blue SEPHAROSE® Fast Flow (Pharmacia), a dye ligand affinity column; S-SEPHAROSE® Fast Flow (Pharmacia), a cation exchange column; Cu Chelating SEPHAROSE® (Pharmacia), a metal ligand affinity column; Fractogel S (EM Separations, Gibbstown, N.J.), a cation exchange column; and Sephacryl-200 (Pharmacia), a gel filtration column. These chromatographic procedures all yielded low, unsatisfactory levels of purification when operated in 1 mM CHAPS. Subsequent gel filtration chromatography on Sephacryl S-200 in 1 mM CHAPS generated an enzymatically active fraction which eluted over a broad size range rather than the expected ~44 kDa size. Taken together, these results indicated that the LDL proteins were aggregating in solution.

Different LDL samples were therefore evaluated by analytical gel filtration chromatography for aggregation of the PAF-AH activity. Samples from the DEAE pool and of freshly solubilized LDL precipitate were analyzed on Superose 12 (Pharmacia) equilibrated in buffer with 1 mM CHAPS. Both samples eluted over a very broad range of molecular weights with most of the activity eluting above 150 kDa. When the samples were then analyzed on Superose 12 equilibrated with 10 mM CHAPS, the bulk of the activity eluted near 44 kDa as expected for PAF-AH activity. However, the samples contained some PAF-AH activity in the high molecular weight region corresponding to aggregates.

Other samples eluted PAF-AH activity exclusively in the ~44 kDa range when they were subsequently tested by gel filtration. These samples were an LDL precipitate solubilized in 10 mM CHAPS in the presence of 0.5M NaCl and a fresh DEAE pool that was adjusted to 10 mM CHAPS after elution from the DEAE column. These data indicate that at least 10 mM CHAPS is required to maintain non-aggregated PAF-AH. Increase of the CHAPS concentration from 1 mM to 10 mM after chromatography on DEAE but prior to subsequent chromatographic steps resulted in dramatic differences in purification. For example, the degree of PAF-AH purification on S-SEPHAROSE® Fast Flow was increased from 2-fold to 10-fold. PAF-AH activity bound the Blue SEPHAROSE® Fast Flow column irreversibly in 1 mM CHAPS, but the column provided the highest level of purification in 10 mM CHAPS. The DEAE chromatography was not improved with prior addition of 10 mM CHAPS.

Chromatography on Cu Chelating SEPHAROSE® after the Blue Sepharose Fast Flow column concentrated PAF-AH activity 15-fold. It was also determined that PAF-AH activity could be recovered from a reduced SDS-polyacrylamide gel, as long as samples were not boiled. The activity of material eluted from the Cu Chelating SEPHAROSE® column when subjected to SDS-polyacrylamide gel electrophoresis coincided with a major protein band when the gel was silver stained.

B. PAF-AH Purification Protocol

The novel protocol utilized to purify PAF-AH for amino acid sequencing therefore comprised the following steps which were performed at 4° C. Human plasma was divided into 900 ml aliquots in 1 liter NALGENE® bottles and adjusted to pH 8.6. LDL particles were then precipitated by adding 90 ml of 3.85% sodium phosphotungstate followed by 23 ml of 2M $MgCl_2$. The plasma was then centrifuged for 15 minutes at 3600 g. Pellets were resuspended in 800 ml of 0.2% sodium citrate. LDL was precipitated again by adding 10 g NaCl and 24 ml of 2M $MgCl_2$. LDL particles were pelleted by centrifugation for 15 minutes at 3600 g. This wash was repeated twice. Pellets were then frozen at −20° C. LDL particles from 5 L of plasma were resuspended in 5 L of buffer A (25 mM Tris-HCl, 10 mM CHAPS, pH 7.5) and stirred overnight. Solubilized LDL particles were centrifuged at 3600 g for 1.5 hours. Supernatants were combined and filtered with Whatman 113 filter paper to remove any remaining solids. Solubilized LDL supernatant was loaded on a DEAE SEPHAROSE® Fast Flow column (11 cm×10 cm; 1 L resin volume; 80 ml/minute) equilibrated in buffer B (25 mM Tris-HCl, 1 mM CHAPS, pH 7.5). The column was washed with buffer B until absorbance returned to baseline. Protein was eluted with an 8 L, 0–0.5M NaCl gradient and 480 ml fractions were collected. This step was necessary to obtain binding to the Blue SEPHAROSE® Fast Flow column below. Fractions were assayed for acetylhydrolase activity essentially by the method described in Example 4.

Figure 1:
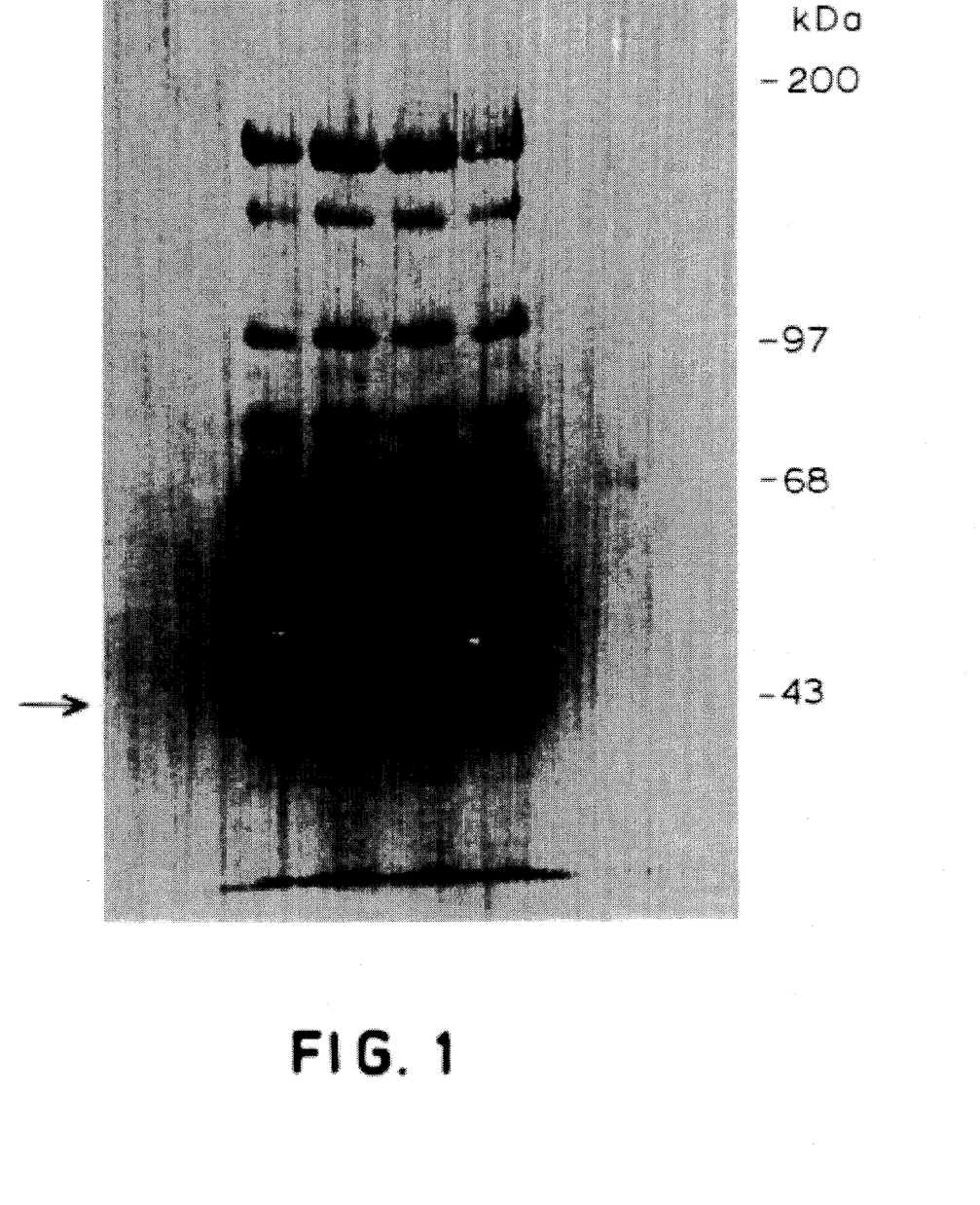
FIG. 1 is a photograph of a PVDF membrane containing PAF-AH purified from human plasma and FIG. 2 is a graph showing the enzymatic activity of recombinant human plasma PAF-AH.

Active fractions were pooled and sufficient CHAPS was added to make the pool ~10 mM CHAPS. The DEAE pool was loaded overnight at 4 ml/minute onto a Blue SEPHAROSE® Fast Flow column (5 cm×10 cm; 200 ml bed volume) equilibrated in buffer A containing 0.5M NaCl. The column was washed with the equilibration buffer at 16 ml/minute until absorbance returned to baseline. PAF-AH activity was step eluted with buffer A containing 0.5M KSCN (a chaotropic salt) at 16 ml/minute and collected in 50 ml fractions. This step resulted in greater than 1000-fold purification. Active fractions were pooled, and the pool was adjusted to pH 8.0 with 1M Tris-HCl pH 8.0. The active pool from Blue SEPHAROSE® Fast Flow chromatography was loaded onto a Cu Chelating SEPHAROSE® column (2.5 cm×2 cm; 10 ml bed volume; 4 ml/minute) equilibrated in buffer C [25 mM Tris-HCl, 10 mM CHAPS, 0.5M NaCl, pH 8.0 (pH 7.5 also worked)], and the column was washed with 50 ml buffer C. PAF-AH activity was eluted with 100 ml 50 mM imidazole in buffer C and collected in 10 ml fractions. Fractions containing PAF-AH activity were pooled and dialyzed against buffer A. In addition to providing a 15-fold concentration of PAF-AH activity, the Cu Chelating SEPHAROSE® column gave a small purification. The Cu Chelating SEPHAROSE® pool was reduced in 50 mM DTT for 15 minutes at 37° C. and loaded onto a 0.75 mM, 7.5% polyacrylamide gel. Gel slices were cut every 0.5 cm and placed in disposable microfuge tubes containing 200 µl 25 mM Tris-HCl, 10 mM CHAPS, 150 mM NaCl. Slices were ground up and allowed to incubate overnight at 4° C. The supernatant of each gel slice was then assayed for PAF-AH activity to determine which protein band on SDS-PAGE contained PAF-AH activity. PAF-AH activity was found in an ~44 kDa band. Protein from a duplicate gel was electrotransferred to a PVDF membrane (Immobilon-P, Millipore) and stained with Coomassie Blue. A photograph of the PVDF membrane is presented in FIG. 1.

As presented in Table I below, approximately 200 µg PAF-AH was purified $2×10^6$-fold from 5 L human plasma. In comparison, a $3×10^4$-fold purification of PAF-AH activity is described in Stafforini et al. (1987), supra.

TABLE 1

| Sample | Vol. (ml) | Activity (cpm × $10^6$) | Total Activity (cpm × $10^9$) | Prot. Conc. (mg/ml) | Specific Activity (cpm × $10^6$) | % Recovery Step | % Recovery Cum. | Fold Purification Step | Fold Purification Cum. |
|---|---|---|---|---|---|---|---|---|---|
| Plasma | 5000 | 23 | 116 | 62 | 0.37 | 100 | 100 | 1 | 1 |
| LDL | 4500 | 22 | 97 | 1.76 | 12 | 84 | 84 | 33 | 33 |
| DEAE | 4200 | 49 | 207 | 1.08 | 46 | 212 | 178 | 3.7 | 124 |
| Blue | 165 | 881 | 14 | 0.02 | 54200 | 70 | 126 | 1190 | $1.5 × 10^5$ |
| Cu | 12 | 12700 | 152 | 0.15 | 82200 | 104 | 131 | 1.5 | $2.2 × 10^5$ |
| SDS-PAGE | — | — | — | — | — | — | — | ~10 | $2.2 × 10^6$ |

In summary, the following steps were unique and critical for successful purification of plasma PAF-AH for microsequencing: (1) solubilization and chromatography in 10 mM CHAPS, (2) chromatography on a blue ligand affinity column such as Blue SEPHAROSE® Fast Flow, (3) chromatography on a Cu ligand affinity column such as Cu Chelating SEPHAROSE®, and (4) elution of PAF-AH from SDS-PAGE.

EXAMPLE 2

For amino acid sequencing, the ~44 kDa protein band from the PAF-AH-containing PVDF membrane described in Example 1 was excised and sequenced using an Applied Biosystems 473A Protein sequencer. N-terminal sequence analysis of the ~44 kDa protein band corresponding to the PAF-AH activity indicated that the band contained two major sequences and two minor sequences. The ratio of the two major sequences was 1:1 and it was therefore difficult to interpret the sequence data.

To distinguish the sequences of the two major proteins which had been resolved on the SDS gel, a duplicate PVDF membrane containing the ~44 kDa band was cut in half such that the upper part and the lower part of the membrane were separately subjected to sequencing.

The N-terminal sequence obtained for the lower half of the membrane was:

FKDLGEENFKALVLIAF                     SEQ ID NO: 1

A search of protein databases revealed this sequence to be a fragment of human serum albumin. The upper half of the same PVDF membrane was also sequenced and the N-terminal amino acid sequence determined was:

IQVLMAAAQFGQTKIP                      SEQ ID NO: 2

This sequence did not match any protein in the databases searched and was different from the N-terminal amino acid sequence:

MKPLVVFVLGG                           SEQ ID NO: 3 which was reported for erythrocyte cytoplasmic PAF-AH in Stafforini et al. (1993), supra. The novel sequence (SEQ ID NO: 2) was utilized for cDNA cloning of human plasma PAF-AH as described below in Example 3.

EXAMPLE 3

A full length clone encoding human plasma PAF-AH was isolated from a macrophage cDNA library.

A. Construction of a Macrophage cDNA Library

Poly A$^+$ RNA was harvested from peripheral blood monocyte-derived macrophages. Double-stranded, blunt-ended cDNA was generated using the Invitrogen Copy Kit (San Diego, Calif.) and BstXI adapters were ligated to the cDNA prior to insertion into the mammalian expression vector, pRc/CMV (Invitrogen). The resulting plasmids were introduced into E. coli strain XL-1 Blue by electroporation. Transformed bacteria were plated at a density of approximately 3000 colonies per agarose plate on a total of 978 plates. Plasmid DNA prepared separately from each plate was retained in individual pools and was also combined into larger pools representing 300,000 clones each.

B. Library-Screening by PCR

The macrophage library was screened by the polymerase chain reaction utilizing a degenerate antisense oligonucleotide PCR primer based on the novel N-terminal amino acid sequence described in Example 2. The sequence of the primer is set out below in IUPAC nomenclature and where "I" is an inosine.

5' ACATGAAICGGIATCYTFIGTYTGICCRAA 3'SEQ ID NO: 4

The codon choice tables of Wada et al., *Nuc. Acids Res.*, 19S: 1981–1986 (1991) were used to select nucleotides at the third position of each codon of the primer. The primer was used in combination with a primer specific for either the SP6 or T7 promoter sequences, both of which flank the cloning site of pRc/CMV, to screen the macrophage library pools of 300,000 clones. All PCR reactions contained 100 ng of template cDNA, 1 µg of each primer, 0.125 mM of each dNTP, 10 mM Tris-HCl pH 8.4, 50 mM MgCl$_2$ and 2.5 units of Taq polymerase. An initial denaturation step of 94° C. for four minutes was followed by 30 cycles of amplification of 1 minute at 94° C., 1 minute at 60° C. and 2 minutes at 72° C. The resulting PCR product was cloned into pBluescript SK$^-$ (Stratagene, La Jolla, Calif.) and its nucleotide sequence determined by the dideoxy chain termination method. The PCR product contained the sequence predicted by the novel peptide sequence and corresponds to nucleotides 1 to 331 of SEQ ID NO: 7.

The PCR primers set out below, which are specific for the cloned PCR fragment described above, were then designed for identifying a full length clone.

Sense Primer (SEQ ID NO: 5)
5' TATTTCTAGAAGTGTGGTGGAACTCGCTGG 3'
Antisense Primer (SEQ ID NO: 6)
5' CGATGAATTCAGCTTGCAGCAGCCATCAGTAC 3'

PCR reactions utilizing the primers were performed as described above to first screen the cDNA pools of 300,000 clones and then the appropriate subset of the smaller pools of 3000 clones. Three pools of 3000 clones which produced a PCR product of the expected size were then used to transform bacteria.

C. Library Screening by Hybridization

DNA from the transformed bacteria was subsequently screened by hybridization using the original cloned PCR fragment as a probe. Colonies were blotted onto nitrocellulose and prehybridized and hybridized in 50% formamide, 0.75M sodium chloride, 0.075M sodium citrate, 0.05M sodium phosphate pH 6.5, 1% polyvinyl pyrolidine, 1% Ficoll, 1% bovine serum albumin and 50 ng/ml sonicated salmon sperm DNA. The hybridization probe was labeled by random hexamer priming. After overnight hybridization at 42° C., blots were washed extensively in 0.03M sodium chloride, 3 mM sodium citrate, 0.1% SDS at 42° C. The nucleotide sequence of 10 hybridizing clones was determined. One of the clones, clone sAH 406-3, contained the sequence predicted by the original peptide sequence of the PAF-AH activity purified from human plasma. The DNA and deduced amino acid sequences of the human plasma PAF-AH are set out in SEQ ID NOs: 7 and 8, respectively.

Clone sAH 406-3 contains a 1.52 kb insert with an open reading frame that encodes a predicted protein of 441 amino acids. At the amino terminus, a relatively hydrophobic segment of 41 residues precedes the N-terminal amino acid (the isoleucine at position 42 of SEQ ID NO: 8) identified by protein microsequencing. The encoded protein may thus have either a long signal sequence or a signal sequence plus an additional peptide that is cleaved to yield the mature functional enzyme. The presence of a signal sequence is one characteristic of secreted proteins. In addition, the protein encoded by clone sAH 406-3 includes the consensus GxSxG motif SEQ 10 NO: 11 (corresponding to amino acids 271–275 of SEQ ID NO: 8) that is believed to contain the active site serine of all known mammalian lipases, microbial lipases and serine proteases. See Chapus et al., *Biochimie*, 70: 1223–1224 (1988) and Brenner, *Nature*, 334: 528–530 (1988).

Table 2 below is a comparison of the amino acid composition of the human plasma PAF-AH of the invention as predicted from SEQ ID NO: 8 and the amino acid composition of the purportedly purified material described by Stafforini et al. (1987), supra.

TABLE 2

|  | Clone sAH 406-3 | Stafforini et al. |
|---|---|---|
| Ala | 26 | 24 |
| Asp & Asn | 48 | 37 |
| Cys | 5 | 14 |
| Glu & Gln | 36 | 42 |
| Phe | 22 | 12 |
| Gly | 29 | 58 |
| His | 13 | 24 |
| Ile | 31 | 17 |
| Lys | 26 | 50 |
| Leu | 40 | 26 |
| Met | 10 | 7 |
| Pro | 15 | 11 |

TABLE 2-continued

|      | Clone sAH 406-3 | Stafforini et al. |
|------|-----------------|-------------------|
| Arg  | 18              | 16                |
| Ser  | 27              | 36                |
| Thr  | 20              | 15                |
| Val  | 13              | 14                |
| Trp  | 7               | Not determined    |
| Tyr  | 14              | 13                |

The amino acid composition of the mature form of the human plasma PAF-AH of the invention and the amino acid composition of the previously purified material that was purportedly the human plasma PAF-AH are clearly distinct.

EXAMPLE 4

To determine whether clone sAH 406-3 encodes a protein having PAF-AH activity, the pRc/CMV expression construct was transiently expressed in COS 7 cells. Three days following transfection by a DEAE Dextran method, COS cell media was assayed for PAF-AH activity.

Cells were seeded at a density of 300,000 cells per 60 mm tissue culture dish. The following day, the cells were incubated in DMEM containing 0.5 mg/ml DEAE dextran, 0.1 mM chloroquine and 5–10/µg of plasmid DNA for 2 hours. Cells were then treated with 10% DMSO in phosphate-buffered saline for 1 minute, washed with media and incubated in DMEM containing 10% fetal calf serum previously treated with diisopropyl fluorophosphate (DFP) to inactivate endogenous bovine serum PAF-AH. After 3 days of incubation, media from transfected cells were assayed for PAF-AH activity. Assays were conducted in the presence and absence of either 10 mM EDTA or 1 mM DFP to determine whether the recombinant enzyme was calcium-independent and inhibited by the serine esterase inhibitor DFP as previously described for plasma PAF-AH by Stafforini et al. (1987), supra. Negative controls included cells transfected with pRc/CMV either lacking an insert or having the sAH 406-3 insert in reverse orientation.

PAF-AH activity in transfectant supernatants was determined by the method of Stafforini et al. (1990), supra, with the following modifications. Briefly, PAF-AH activity was determined by measuring the hydrolysis of $^3$H-acetate from [acetyl-$^3$H] PAF (New England Nuclear, Boston, Mass.). The aqueous free $^3$H-acetate was separated from labeled substrate by reversed-phase column chromatography over octadecylsilica gel cartridges (Baker Research Products, Phillipsburg, Pa.). Assays were carried out using 10 µl transfectant supernatant in 0.1M Hepes buffer, pH 7.2, in a reaction volume of 50 µl. A total of 50 pmoles of substrate were used per reaction with a ratio of 1:5 labeled: cold PAF. Reactions were incubated for 30 minutes at 37° C. and stopped by the addition of 40 µl of 10M acetic acid. The solution was then washed through the octadecylsilica gel cartridges which were then rinsed with 0.1M sodium acetate. The aqueous eluate from each sample was collected and counted in a liquid scintillation counter for one minute. Enzyme activity was expressed in counts per minute.

Figure 2:
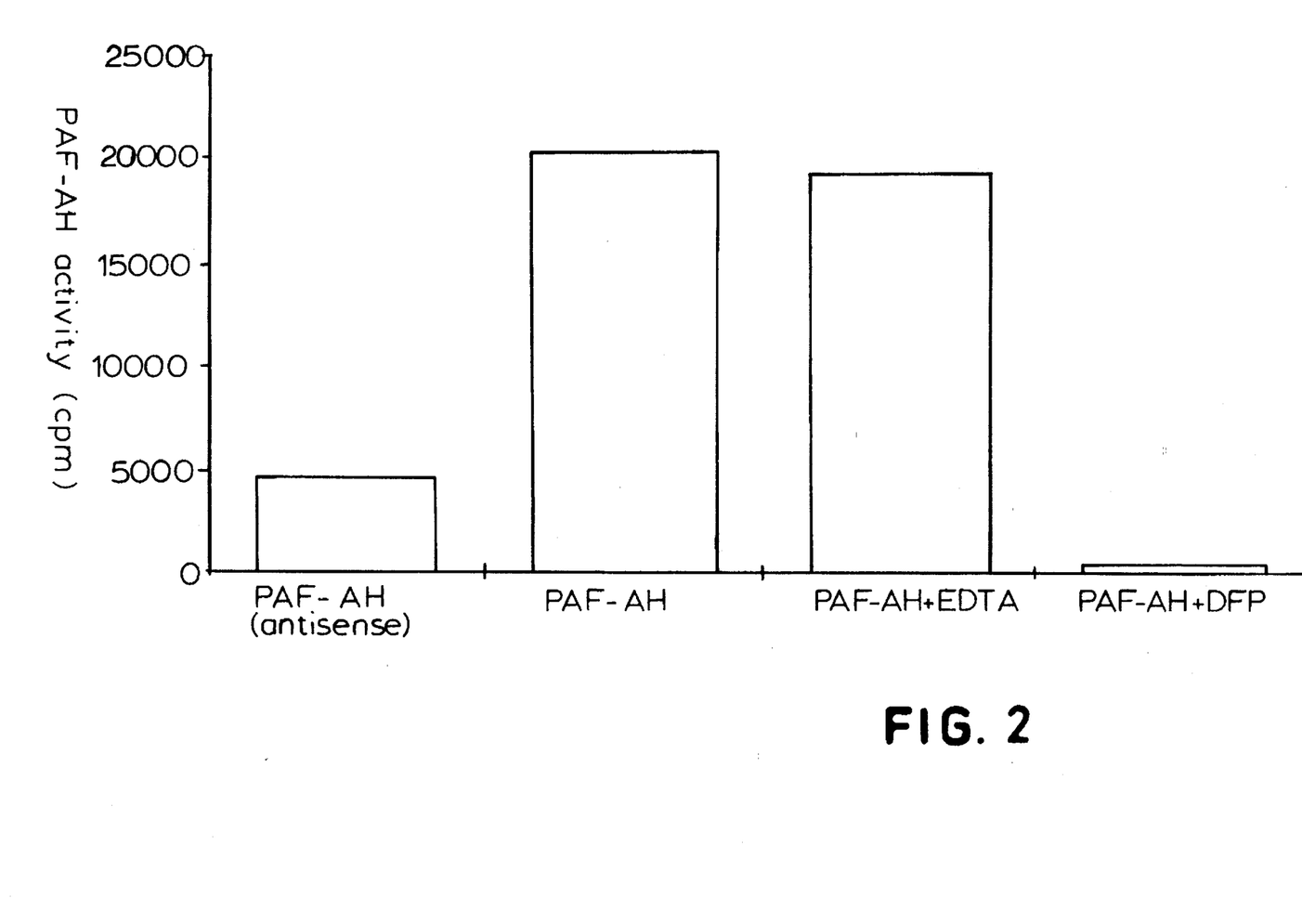

As shown in FIG. 2, media from cells transfected with sAH 406-3 contained PAF-AH activity at levels 4-fold greater than background. This activity was unaffected by the presence of EDTA but was abolished by 1 mM DFP. These observations demonstrate that clone sAH 406-3 encodes an activity consistent with the human plasma enzyme PAF-AH.

EXAMPLE 5

PCR was used to generate a protein coding fragment of human plasma PAF-AH cDNA from clone sAH 406-3 which was readily amenable to subcloning into an E. coli expression vector. The subcloned segment began at the 5' end of the human gene with the codon that encodes $Ile_{42}$ (SEQ ID NO: 8), the N-terminal residue of the enzyme purified from human plasma. The remainder of the gene through the native termination codon was included in the construct. The 5' sense PCR primer utilized was:

5' TATTCTAGAATT
<u>ATG</u>ATACAAGTATTAATGGCTGCTGCAAG SEQ ID NO: 9

3' and contained an XbaI cloning site as well as a translation initiation codon (underscored). The 3' antisense primer utilized was:

5' ATTGATATCCTAATFGTATITCTCTATFCCTG SEQ ID NO: 10 and encompassed the termination codon of sAH 406-3 and contained an EcoRV cloning site. PCR reactions were performed essentially as described in Example 3. The resulting PCR product was digested with XbaI and EcoRV and subcloned into a pBR322 vector containing the Trp promoter immediately upstream of the cloning site. E. coli strain XL-1 Blue was transformed with the expression construct and cultured in L broth containing 100 µg/ml of carbenicillin. Transformants from overnight cultures were pelleted and resuspended in lysis buffer containing 50 mM Tris-HCl pH 7.5, 50 mM NaCl, 10 mM CHAPS, 1 mM EDTA, 100 µg/ml lysozyme, and 0.05 trypsin-inhibiting units (TIU)/ml Aprotinin. Following a 1 hour incubation on ice and sonication for 2 minutes, the lysates were assayed for PAF-AH activity by the method described in Example 4. E. coli transformed with the expression construct generated a product with PAF-AH activity. See Table 3 in Example 6.

EXAMPLE 6

Recombinant human plasma PAF-AH expressed in E. coli was purified to a single Coomassie-stained SDS-PAGE band by a method similar to that described in Example 1 for native PAF-AH.

The following purification steps were performed at 4° C. Pellets from 50 ml PAF-AH producing E. coli cultures were lysed as described in Example 5. Solids were removed by centrifugation at 10,000 g for 20 minutes. The supernatant was loaded at 0.8 ml/minute onto a Blue SEPHAROSE® Fast Flow column (2.5 cm×4 cm; 20 ml bed volume) equilibrated in buffer D (25 mM Tris-HCl, 10 mM CHAPS, 0.5M NaCl, pH 7.5). The column was washed with 100 ml buffer D and eluted with 100 ml buffer A containing 0.5M KSCN at 3.2 ml/minute. A 15 ml active fraction was loaded onto a 1 ml Cu Chelating SEPHAROSE® column equilibrated in buffer D. The column was washed with 5 ml buffer D followed by elution with 5 ml of buffer D containing 100 mM imidazole with gravity flow. Fractions containing PAF-AH activity were analyzed by SDS-PAGE.

The results of the purification are shown in Table 3 wherein a unit equals µmol PAF hydrolysis per hour. The purification product obtained at 4° C. appeared on SDS-PAGE as a single intense band below the 43 kDa marker with some diffuse staining directly above and below it. The recombinant material is significantly more pure and exhibits greater specific activity when compared with PAF-AH preparations from plasma as described in Example 1.

TABLE 3

| Sample | Volume (ml) | Activity (units/ml) | Total Act. (units × 10³) | Prot Conc (mg/mL) | Specific Activity (units/mg) | % Recovery Step | % Recovery Cum. | Fold Purification Step | Fold Purification Cum. |
|---|---|---|---|---|---|---|---|---|---|
| Lysate | 4.5 | 989 | 4451 | 15.6 | 63 | 100 | 100 | 1 | 1 |
| Blue | 15 | 64 | 960 | 0.07 | 914 | 22 | 22 | 14.4 | 14.4 |
| Cu | 1 | 2128 | 2128 | 0.55 | 3869 | 220 | 48 | 4.2 | 61 |

When the same purification protocol was performed at ambient temperature, in addition to the band below the 43 kDa marker, a group of bands below the 29 kDa marker correlated with PAF-AH activity of assayed gel slices. These lower molecular weight bands may be proteolytic fragments of PAF-AH that retain enzymatic activity.

EXAMPLE 7

A preliminary analysis of expression patterns of human plasma PAF-AH mRNA in human tissues was conducted by Northern blot hybridization.

RNA was prepared from human brain, heart, kidney, placenta, thymus and tonsil using RNA Stat 60 (Tel-Test "B", Friendswood, Tex.). Additionally, RNA was prepared from the human hematopoietic precursor-like cell line, THP-1 (ATCC TIB 202), which was induced to differentiate to a macrophage-like phenotype using the phorbol ester phorbolmyristylacetate (PMA). Tissue RNA and RNA prepared from THP-1 cells prior to and 1 to 3 days after induction were electrophoresed through a 1.2% agarose formaldehyde gel and subsequently transferred to a nitrocellulose membrane. The full length human plasma PAF-AH cDNA, sAH 406-3, was labelled by random priming and hybridized to the membrane under conditions identical to those described in Example 3 for library screening.

Initial results indicate that the PAF-AH probe hybridized to a 1.8 kb band in the thymus, tonsil, and to a lesser extent, the placental RNA. In addition, expression of the human plasma PAF-AH transcript was observed in the THP-1 cell RNA at 1 day but not 3 days following induction.

While the present invention has been described in terms of specific embodiments, it is understood that variations and modifications will occur to those skilled in the art. Accordingly, only such limitations as appear in the appended claims should be placed on the invention.

We claim:

1. A purified and isolated polynucleotide consisting of a polynucleotide encoding the plasma platelet-activating factor acetylhydrolase (PAF-AH) amino acid sequence set out in SEQ ID NO: 8.

2. A DNA according to claim 1.

3. The DNA of claim 2 which is a cDNA or a biological replica thereof.

4. The DNA of claim 2 which consists of the sequence set out in SEQ ID NO: 7.

5. A purified and isolated polynucleotide consisting of a polynucleotide encoding amino acids 42 to 441 of SEQ ID NO: 8.

6. The DNA of claim 2 which is a genomic DNA or a biological replica thereof.

7. A purified and isolated RNA transcript of the genomic DNA of claim 6.

8. A purified and isolated DNA consisting of a DNA encoding platelet-activating factor acetylhydrolase (PAF-AH) enzyme capable of hydrolyzing $^{3}$H-acetate from PAF selected from the group consisting of:

(a) a DNA having the sequence set out in SEQ ID NO: 7;

(b) a DNA which hybridizes under stringent conditions to the non-coding strand of the DNA of (a); and     (c) a DNA which, but for the redundancy of the genetic code, would hybridize under stringent conditions to the non-coding strand of said DNA sequence of (a) or (b).

9. The DNA of claim 6 further comprising an endogenous expression control DNA sequence.

10. A vector comprising a DNA according to claim 2 or 8.

11. The vector of claim 10 wherein said DNA is operatively linked to an expression control DNA sequence.

12. A host cell stably transformed with a DNA according to claim 2 or 8 in a manner allowing expression in said host cell of PAF-AH.

13. A method for producing PAF-AH, said method comprising growing a host cell according to claim 12 in a suitable nutrient medium and isolating PAF-AH from said cell or the medium of its growth.

14. A method for purifying active PAF-AH enzyme from *E. coli* transformed with a DNA according to claim 2 or 8, said method comprising the steps of:

(a) preparing a centrifugation supernatant from lysed *E. coli* producing PAF-AH enzyme;

(b) applying said centrifugation supernatant to a blue dye ligand affinity column;

(c) eluting PAF-AH enzyme from said blue dye ligand affinity column using a buffer comprising 10 mM CHAPS and a chaotropic salt;

(d) applying said eluate from said blue dye ligand affinity column to a Cu ligand affinity column; and     (e) eluting PAF-AH enzyme from said Cu ligand affinity column using a buffer comprising 10 mM CHAPS and imidazole.

15. The method of claim 14 wherein the buffer of step (c) is 25 mM Tris-HCl, 10 mM CHAPS, 0.5M KSCN, pH 7.5 and the buffer of step (e) is 25 mM Tris-HCl, 10 mM CHAPS, 0.5M NaCl, 100 mM imidazole, pH 7.5.

* * * * *

UNITED STATES PATENT AND TRADEMARK OFFICE
CERTIFICATE OF CORRECTION

PATENT NO. : 5,532,152        Page 1 of 2
DATED     : July 2, 1996
INVENTORS : Cousens et al.

It is certified that error appears in the above-identified patent and that said Letters Patent is hereby corrected as shown below:

column 1, line 27 replace "34:69 1-701" with --34:691-701--;

column 3, line 34 replace "10mm" with --10mM--;

column 3, line 38 replace "10mm" with --10mM--;

column 3, line 40 replace "PAFAH" with --PAF-AH--;

column 9, line 45 replace "ACATGAATICGGIATCYTFIGTYTGICCRAA" with --ACATGAATTCGGIATCYTTIGTYTGICCRAA--;

column 10, line 42 replace "SEQ 10 NO:" with --SEQ ID NO:--;

column 11, line 24 replace "5-10/µg" with --5-10 µg--;

column 12, line 16 replace "ATTGATATCCTAATFGTATITCTCTATFCCTG" with --ATTGATATCCTAATTGTATTTCTCTATTCCTG 3'--;

column 12, line 32 the sentence "E. coli transformed..." should start a new paragraph; and

UNITED STATES PATENT AND TRADEMARK OFFICE
CERTIFICATE OF CORRECTION

PATENT NO. : 5,532,152

DATED : July 2, 1996

INVENTOR(S) : Cousens et al.

It is certified that error appears in the above-indentified patent and that said Letters Patent is hereby corrected as shown below:

column 23, line 39 before "PAF" insert --[acetyl-$^3$H]--.

Signed and Sealed this

Seventeenth Day of June, 1997

Attest:

BRUCE LEHMAN

Attesting Officer

Commissioner of Patents and Trademarks